(12) United States Patent
Hines

(10) Patent No.: US 10,322,545 B1
(45) Date of Patent: Jun. 18, 2019

(54) MEASURING INK STREAM DEPOSITION RATE OF AN AEROSOL-JET PRINTER

(71) Applicant: The United States of America as represented by the Director, National Security Agency, Washingon, DC (US)

(72) Inventor: Daniel R. Hines, Damascus, MD (US)

(73) Assignee: The United States of America as represented by the Director, National Security Agency, Washington, DC (US)

( * ) Notice: Subject to any disclaimer, the term of this patent is extended or adjusted under 35 U.S.C. 154(b) by 90 days.

(21) Appl. No.: 15/673,663

(22) Filed: Aug. 10, 2017

Related U.S. Application Data

(60) Provisional application No. 62/384,877, filed on Sep. 8, 2016.

(51) Int. Cl.
*B41J 29/38* (2006.01)
*B29C 64/393* (2017.01)
*B33Y 50/02* (2015.01)

(52) U.S. Cl.
CPC ............ *B29C 64/393* (2017.08); *B33Y 50/02* (2014.12); *B41J 29/38* (2013.01)

(58) Field of Classification Search
None
See application file for complete search history.

(56) References Cited

U.S. PATENT DOCUMENTS

| 2011/0177489 A1* | 7/2011 | Takahashi | B01L 3/0262 435/3 |
| 2016/0200927 A1* | 7/2016 | Wu | C09D 11/101 347/20 |
| 2016/0221230 A1* | 8/2016 | Mita | B29C 64/112 |

* cited by examiner

*Primary Examiner* — Matthew Luu
*Assistant Examiner* — Tracey M McMillion

(57) ABSTRACT

A method is disclosed for calibrating a deposition rate in an aerosol jet printer. The method includes providing a substrate defining an array of wells, each defining a volume. The method also includes defining a toolpath such that a dispensing nozzle passes over the wells. The method also includes defining a dwell time such that the nozzle remains centered above each well for an amount of time equal to the dwell time, after which the nozzle follows the toolpath to be centered over the following well. The dwell time defines a deposition rate based on the volume of the wells. The method also includes causing the nozzle to move along the toolpath, depositing material into the wells. The method also includes observing one of overfilling and underfilling and adjusting dispensing parameters to effect a modified deposition rate, until the wells are being filled to within a tolerance of exactly full.

14 Claims, 3 Drawing Sheets

MEASURING INK STREAM DEPOSITION RATE OF AN AEROSOL-JET PRINTER

CROSS REFERENCE TO RELATED APPLICATIONS

This application claims priority to provisional patent application Ser. No. 62/384,877, filed Sep. 8, 2016, titled "Measuring Ink Stream Deposition Rate of an Aerosol-Jet Printer," naming Daniel Hines as sole inventor, the contents of which are hereby incorporated by reference herein in their entirety.

FIELD OF INVENTION

The present invention relates, in general, to aerosol jet printers and, in particular, to methods of measuring ink stream deposition rates.

BACKGROUND OF THE INVENTION

Aerosol jet printing is an emerging additive manufacturing, direct-write materials deposition method. Unlike other direct-write printing methods such as syringe/extrusion and ink-jet printing, aerosol-jet printing can be performed with a working distance in the range of 1-5 mm. Therefore, the quality of a printed feature is much less dependent on the topology of the surface onto which the ink is deposited/printed. With aerosol-jet printing the ink stream width also can be controlled from approximately 10 µm up to 200 µm and, for high volume systems, into the millimeter range.

Prior art approaches have included measuring material output by printing some amount of ink into a weighing pan over a given time and weighing the result. The deposition rate may then be calculated by noting what weight of ink is deposited per unit time, and determining the volume of the deposited ink based on the weight of the deposited ink and a known density of the deposited ink. This approach has several drawbacks. One drawback is that the process can be awkward and time-consuming. The weighing pan must be installed, the filling performed, the weighing pan removed, and then weighed. Furthermore, the printing into the weighing pan must be performed for a certain minimum period of time in order to deposit a certain minimum amount of ink, in order to provide reasonable accuracy to deposition rate calculations based on the elapsed time and total weight. At small scales, with small deposition rates, it may take a while to complete this process—as much as between a half an hour and an hour, with even some of the fastest deposition rates requiring on the order of ten minutes. Furthermore, this process may need to be repeated from start to finish several times to account for variability in the flow rate and uncertainty in the measurements.

SUMMARY

A first embodiment of the present invention is a method of calibrating a deposition rate in an aerosol jet printer. The method includes providing a substrate having a surface. The substrate defines an array of wells relative to the surface, each of the wells defining a common known volume. The method also includes defining a toolpath for the aerosol-jet printer such that a dispensing nozzle of the aerosol jet printer passes sequentially over each of the wells of the array of wells defined by the substrate. The method also includes defining a dwell time for the toolpath, such that the dispensing nozzle, while following the toolpath, remains centered above each well for an amount of time equal to the dwell time, after which the dispensing nozzle follows the toolpath to be centered over the following well. The dwell time defines a target deposition rate based on the common known volume of the wells. The method also includes causing the dispensing nozzle to move along the toolpath, depositing material into the wells at an initial deposition rate. The method also includes observing one of overfilling and underfilling of the wells and repeatedly adjusting dispensing parameters to effect a modified deposition rate, until the wells are being filled to within a tolerance of exactly full.

In a related embodiment, wherein the wells are cylindrical. In a further related embodiment, wherein the cylinders have a diameter of 200 µm and a depth of 100 µm.

In another related embodiment, the substrate may be marked with alignment marks to guide the movement of the nozzle in being centered over the wells. The dispensing parameters may include a process gas flow rate for aerosol production. The deposited material may be one of a silver-based ink and a polyimide-based ink.

In another related embodiment, observing one of overfilling and underfilling of the wells includes monitoring the depositing of material into the wells with a camera, and determining, using image-recognition software processing image data generated by the camera, whether a transition occurs in the deposited ink from a concave surface to a convex surface. In the event the transition did not occur before the nozzle continues along the toolpath to the next well, it is determined that underfilling occurred. In the event material was deposited for more than a buffer time after the transition occurred it is determined that overfilling occurred.

A second embodiment of the present invention is a method of determining a deposition rate in an aerosol-jet printer. The method includes providing a substrate having a flat surface. The substrate defines an array of wells relative to the flat surface, each of the wells defining a common known volume. The method also includes defining a toolpath for the aerosol-jet printer such that a dispensing nozzle of the aerosol-jet printer passes sequentially over each of the wells of the array of wells defined by the substrate. The method also includes defining a dwell time for the toolpath, such that the dispensing nozzle, while following the toolpath, remains centered above each well for an amount of time equal to the dwell time, after which the dispensing nozzle follows the toolpath to be centered over the following well. The method also includes causing the dispensing nozzle to move along the toolpath, depositing material into the wells at a deposition rate. The method also includes observing one of overfilling and underfilling of the wells and repeatedly adjusting the dwell time to effect a modified deposition volume for each well, until the wells are being filled to within a tolerance of exactly full during the adjusted dwell time. The method also includes determining the deposition rate based on the common known volume of the wells and the adjusted dwell time.

DETAILED DESCRIPTION

In accordance with embodiments of the present invention, an array of inkwells can be used to quantitatively measure the ink stream deposition rate of an aerosol jet printer while the machine is running. Previous approaches to measuring the ink stream deposition rate involved a qualitative visual inspection of lines during printing, or measuring a feature after it has been printed. Use of inkwells as disclosed herein allows for the ink stream deposition rate to be measured quantitatively at any time while the ink stream is running. Unlike these prior approaches which could require significant operation time, often on the order of 10-50 minutes, embodiments of the present invention have been employed to consistently calibrate ink stream deposition rates in as little as seconds.

In accordance with an embodiment of the present invention, an array of wells, or holes, can be fabricated into the surface of a substrate, for example by performing photolithography on the surface of a silicon wafer. The array may include, for example, cylinders each having a diameter of 200 micrometers, etched 100 micrometers deep, with 600 micrometers between centers. In other embodiments the cylinders maybe a different diameter and/or a different depth. For example, diameters of 400 micrometers, 100 micrometers, and 50 micrometers all have been used successfully. Well diameters should equal or exceed a width of the deposition stream. For example, an ink deposition stream that is wider than the inkwell into which it is printing will not provide reliable results, as not all of the ink stream is being captured in the inkwell. Well diameters also should not greatly exceed the width of the deposition stream, so that the wells fill evenly. Ideally, the deposited material should uniformly wet the sidewalls of the wells. Lower viscosity inks may spread faster and thus work with slightly wider sidewalls, whereas thick deposited materials may tend to pillar more, and thus will require narrower sidewalls.

Similarly, alternate well depths, such as 200 micrometers or more are also possible. Deeper wells will result in longer fill times, and thus greater accuracy in calculated deposition rates. On the other hand, shallower wells will result in shorter fill times, allowing for the calibration and/or rate calculation operations to be completed more quickly. Additionally, substrates with shallower wells may be manufactured more quickly.

Some embodiments have used cylindrical well shapes, but alternate shapes are possible also. For example, conical wells, square wells, and semispherical wells all may be employed if desired.

Figure 3:
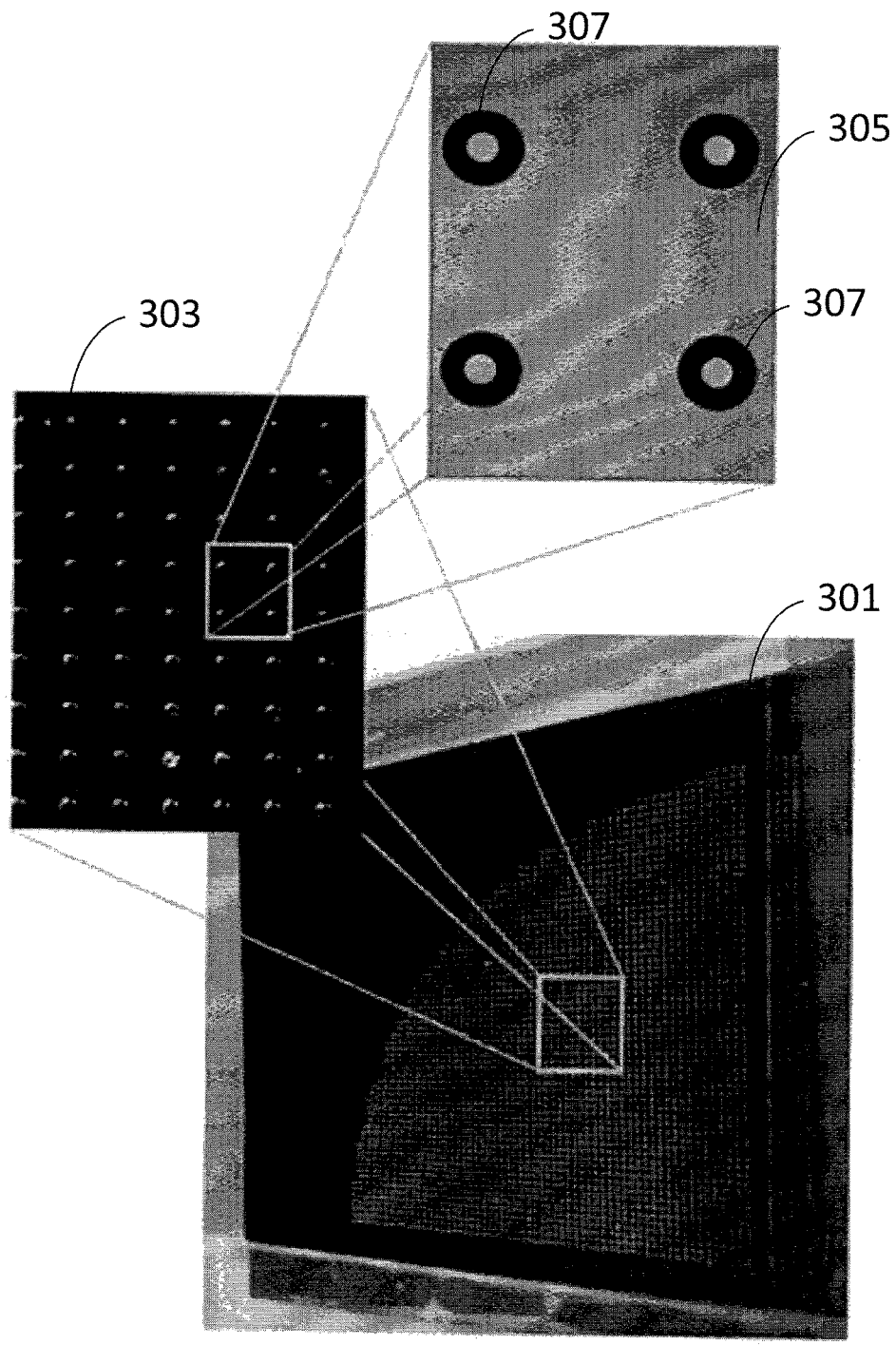
FIG. 3 is a diagram showing views of a substrate containing an array of inkwells in accordance with an embodiment of the present invention, at various levels of magnification.

An example of a substrate with an array of inkwells can be seen in FIG. 3. A substrate 301 has an array of inkwells etched into its surface. A magnified view 303 of a subsection of the substrate 301 shows that a rectangular grid layout of the wells is used in this embodiment. A further magnified view 305 shows a closer view of a subsection of the magnified view 303, in which the individual inkwells 307 are plainly visible.

Adding appropriate alignment marks, the array of wells can be lined up on the aerosol-jet printer and the printer can be controlled to move to the center of each well, open the shutter, and print into each well. The precise amount of time spent printing into each well may be preset, e.g., based on an estimated approximate deposition rate, and the printing process may be adjusted during printing so that each well is filled precisely just as the shutter is closed. The printing process may be adjusted during execution by adjusting printing parameters, such as process gas flow rates that are used to adjust the aerosol production, or also by adjusting the total deposition time.

A camera monitoring the deposition process in the well can be used to observe when the top surface of the ink volume printed into the well reaches the top of the ink well, when the curvature of the ink surface changes from concave to convex. This change in curvature is substantially instantaneous and easily visible, which provides a precise control for measuring and establishing the desired ink stream deposition rate. In some embodiments, similarly to how alignment, purging, and flow rate calibration capabilities for an aerosol-jet printer may be built into a control page displayed by control software operating on a computer connected to the printer, a software function also may be included for running the program to fill the ink wells, in order to facilitate measurement and calibration of ink stream deposition rates while running the printer machine. Various inks have been tested and found suitable for use in the processes described above. For example, silver-based inks and polyimide-based inks have been printed into arrays of wells, though other materials also may be used, so long as they can be aerosolized.

Figure 1:
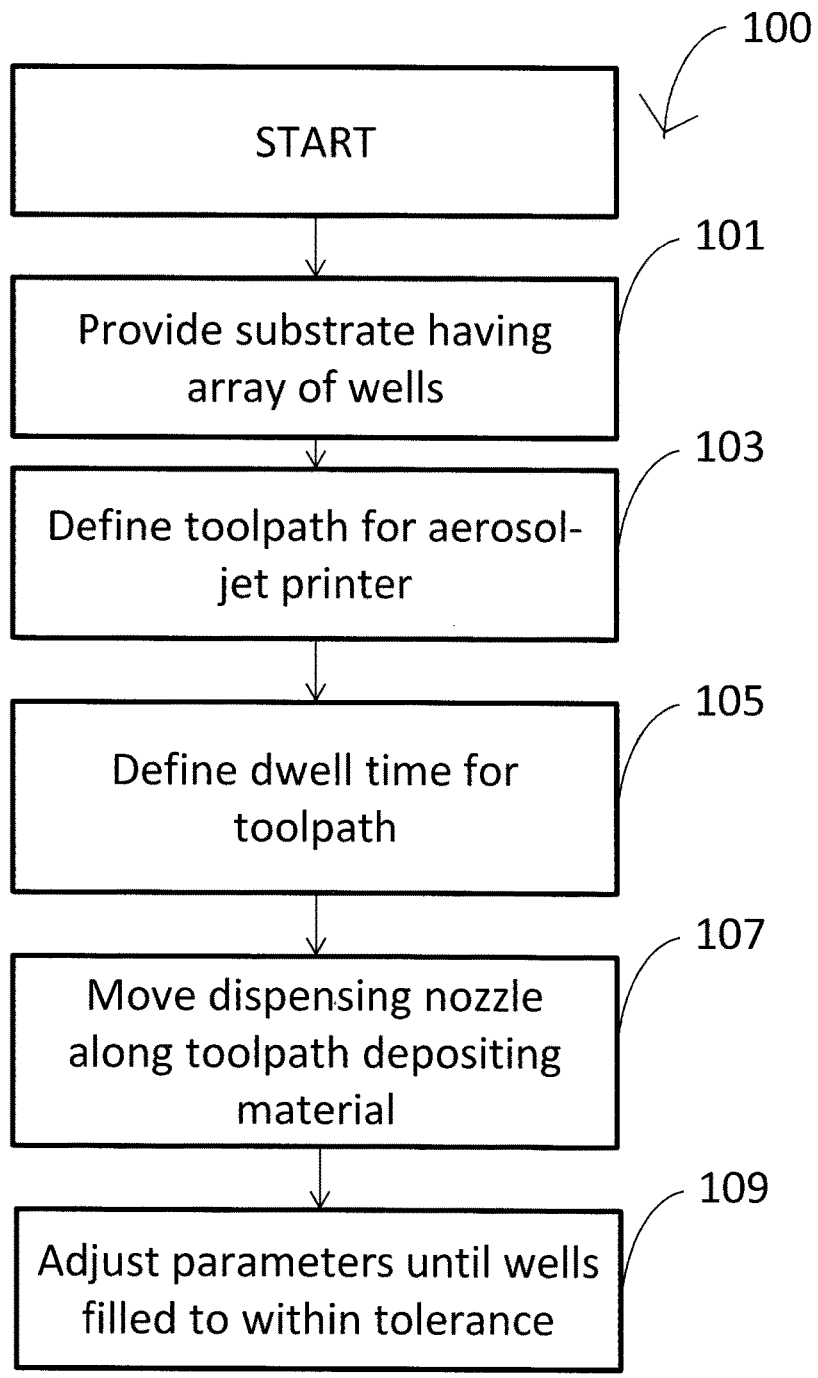
FIG. 1 is a flow chart of a process in accordance with an embodiment of the present invention.

A process 100 in accordance with the present invention is now described with reference to FIG. 1. The process 100 begins at block 101, where a substrate is provided, having an array of wells. The substrate may be a silicon wafer. In other embodiments, the substrate may be polydimethylsiloxane (PDMS). Other materials suitable for fabricating an array of holes of known volume may be used as well. The substrate may have an array of wells formed in it via, for example, photolithography. In other embodiments, an array of wells may be made via a molding process. To verify the geometry and uniformity of these wells, x-ray tomography and optical confocal microscopy also may be used. The process 100 continues at block 103, where a toolpath is defined. The toolpath defines a path of the aerosol-jet printer to be followed during the later portions of the process 100. The process 100 continues at block 105, where a dwell time is defined for the toolpath. The dwell time defines how long the aerosol jet printer will spend centered over any particular well while depositing material into that well prior to continuing along the toolpath to the next well. While blocks 101, 103, and 105 are presented here sequentially, the actions of these blocks may be performed in any order or simultaneously without departing from the scope of the present invention, as each of these actions may be performed independently of the other actions.

Having completed the actions of blocks 101, 103, and 105, the process 100 now continues to block 107, where the dispensing nozzle of the aerosol jet printer moves along the toolpath, depositing material into a series of wells in the substrate, one after the other. In the event that the deposition of material into each well during the dwell time causes each well to be filled approximately full, the deposition rate is already at the target deposition rate and no further calibration is required. However, in the majority of cases this will not be expected to occur. For example, current aerosol jet printing systems may suffer from a gradual drift in deposition rates, independent of any intentional adjustments to deposition rates, and thus after a deposition rate has been calibrated, it can be expected to exhibit a noticeably different deposition rate within hours or even minutes of continued operation.

The process 100 continues at block 109, where printing parameters are adjusted until the wells are being filled to within a tolerance of exactly full. The moving of the dispensing nozzle along the toolpath, which began in block 107, continues while the adjusting of block 109 takes place. If the wells are being overfilled and excess material is spilling out, the parameters are adjusted to reduce the deposition rate. If the wells are being underfilled, for example, if a curvature of the surface of an ink volume does not change from concave to convex, the parameters are adjusted to increase the deposition rate. If the wells are being filled exactly, or approximately full (i.e., the difference between exact filling and actual filling differs by a small amount, such as less than a defined tolerance), then the deposition rate has been calibrated successfully. The calibrated deposition rate is defined by the volume of the wells and the dwell time as is understood in the art.

Figure 2:
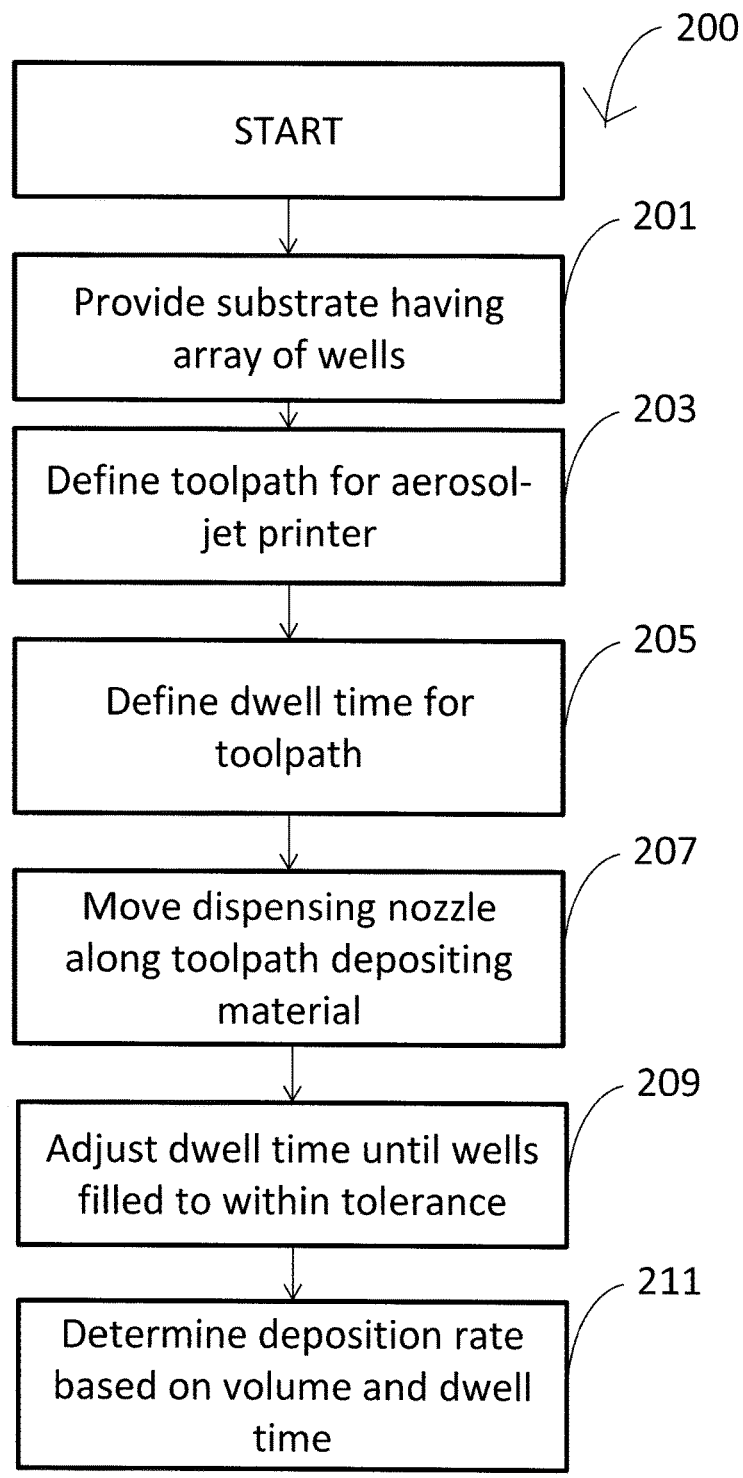
FIG. 2 is a flow chart of a process in accordance with an embodiment of the present invention.

A process 200 in accordance with the present invention is now described with reference to FIG. 2. The process 200, begins at block 201, where a substrate is provided, having an array of wells. The substrate may be a silicon wafer. In other embodiments, the substrate may be polydimethylsiloxane (PDMS). The substrate may have an array of wells formed in it via, for example, photolithography. In other embodiments, an array of wells may be made via a molding process. To verify the geometry and uniformity of these wells, x-ray tomography and optical confocal microscopy also may be used. The process 200 continues at block 203, where a toolpath is defined. The toolpath defines a path of the aerosol-jet printer to be followed during the later portions of the process 200. The process 200 continues at block 205, where a dwell time is defined for the toolpath. The dwell time defines how long the aerosol-jet printer will spend centered over any particular well while depositing material into that well prior to continuing along the toolpath to the next well. While blocks 201, 203, and 205 are presented here sequentially, the actions of these blocks may be performed in any order or simultaneously without departing from the scope of the present invention, as each of these actions may be performed independently of the other actions.

Having completed the actions of blocks 201, 203, and 205, the process 200 now continues to block 207, where the dispensing nozzle of the aerosol jet printer moves along the toolpath, depositing material into a series of wells in the substrate, one after the other. In the event that the deposition of material into each well during the dwell time causes each well to be filled approximately full, the deposition rate is already at the target deposition rate and no further calibration is required. However, in the majority of cases this will not be expected to occur. For example, current aerosol-jet printing systems may suffer from a gradual drift in deposition rates, independent of any intentional adjustments to deposition rates, and thus after a deposition rate has been calibrated, it can be expected to exhibit a noticeably different deposition rate within hours or even minutes of continued operation.

The process 200 continues at block 209, where the dwell time is adjusted until the wells are being filled to within a tolerance of exactly full. The moving of the dispensing nozzle along the toolpath, which began in block 207, continues while the adjusting of block 209 takes place. If the wells are being overfilled and excess material is spilling out, the dwell time is reduced. If the wells are being underfilled, for example, if a curvature of the surface of an ink volume does not change from concave to convex, the dwell time is increased. If the wells are being filled exactly, or approximately full (i.e., the difference between exact filling and actual filling differs by a small amount, such as less than a defined tolerance), then a dwell time has been found that will allow the deposition rate to be calculated successfully.

The process 200 continues at block 211, where the deposition rate is determined based on the volume of the wells and the dwell time. The calculated deposition rate is defined by the volume of the wells and the dwell time as is understood in the art.

Depending on the embodiment, certain acts, events, or functions of any of the methods described herein can be performed in a different sequence, can be added, merged, or left out all together. Not all described acts or events are necessarily required for the practice of any claimed method. Moreover, in certain embodiments, acts or events can be performed concurrently, e.g., through multi-threaded processing, interrupt processing, or multiple processors or processor cores or on other parallel architectures, rather than sequentially.

The various illustrative logical blocks, modules, and steps described in connection with the embodiments disclosed herein can be implemented as electronic hardware, computer software, or combinations of both. To clearly illustrate this interchangeability of hardware and software, various illustrative components, block, modules, and steps have been described above generally in terms of their functionality. Whether such functionality is implemented as hardware or software depends on the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The steps of a method or process described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that may not provide all of the features and benefits set forth herein, as some features can be used or practiced separately from others. The scope of the invention is indicated by the appended claims rather than the foregoing description. All changes which come within the meaning and range of equivalency of the claims are to be embraced within their scope.

I claim:

1. A method of calibrating a deposition rate in an aerosol-jet printer, the method comprising:
    providing a substrate having a surface, wherein the substrate defines an array of wells relative to the surface, each of the wells defining a common known volume;
    defining a toolpath for the aerosol-jet printer such that a dispensing nozzle of the aerosol-jet printer passes sequentially over each of the wells of the array of wells defined by the substrate;
    defining a dwell time for the toolpath, such that the dispensing nozzle, while following the toolpath, remains centered above each well for an amount of time equal to the dwell time, after which the dispensing nozzle follows the toolpath to be centered over the following well,
    wherein the dwell time defines a target deposition rate based on the common known volume of the wells;
    causing the dispensing nozzle to move along the toolpath, depositing material into the wells at an initial deposition rate; and
    observing one of overfilling and underfilling of the wells and repeatedly adjusting dispensing parameters to effect a modified deposition rate, until the wells are being filled to within a tolerance of exactly full;
    wherein observing one of overfilling and underfilling of the wells comprises:
    monitoring the depositing of material into the wells with a camera;
    determining, using image-recognition software processing image data generated by the camera, whether a transition occurs in the deposited ink from a concave surface to a convex surface;
    in the event the transition did not occur before the nozzle continues along the toolpath to the next well, determining that underfilling has occurred; and
    in the event material was deposited for more than a buffer time after the transition occurred, determining that overfilling occurred.

2. A method in accordance with claim 1, wherein the wells are cylindrical.

3. A method in accordance with claim 2, wherein the cylinders have a diameter of 200 µm and a depth of between 100 µm and 200 µm.

4. A method in accordance with claim 1, wherein the substrate is marked with alignment marks to guide the movement of the nozzle in being centered over the wells.

5. A method in accordance with claim 1, wherein the dispensing parameters include a process gas flow rate for aerosol production.

6. A method in accordance with claim 1, wherein the deposited material comprises a metal-based ink.

7. A method in accordance with claim 1, wherein the deposited material comprises a polymer-based ink.

8. A method of determining a deposition rate in an aerosol-jet printer, the method comprising:
    providing a substrate having a surface, wherein the substrate defines an array of wells relative to the surface, each of the wells defining a common known volume;
    defining a toolpath for the aerosol-jet printer such that a dispensing nozzle of the aerosol-jet printer passes sequentially over each of the wells of the array of wells defined by the substrate;
    defining a dwell time for the toolpath, such that the dispensing nozzle, while following the toolpath, remains centered above each well for an amount of time equal to the dwell time, after which the dispensing nozzle follows the toolpath to be centered over the following well,
    causing the dispensing nozzle to move along the toolpath, depositing material into the wells at a deposition rate;
    observing one of overfilling and underfilling of the wells and repeatedly adjusting the dwell time to effect a modified deposition volume for each well, until the wells are being filled to within a tolerance of exactly full during the adjusted dwell time; and
    determining the deposition rate based on the common known volume of the wells and the adjusted dwell time.

9. A method in accordance with claim 8, wherein the wells are cylindrical.

10. A method in accordance with claim 9, wherein the cylinders have a diameter of 200 µm and a depth of 100 µm.

11. A method in accordance with claim 8, wherein the substrate is marked with alignment marks to guide the movement of the nozzle in being centered over the wells.

12. A method in accordance with claim 8, wherein the deposited material comprises a metal-based ink.

13. A method in accordance with claim 8, wherein the deposited material comprises a polymer-based ink.

14. A method in accordance with claim 8, wherein observing one of overfilling and underfilling of the wells comprises:
    monitoring the depositing of material into the wells with a camera;
    determining, using image-recognition software processing image data generated by the camera, whether a transition occurs in the deposited ink from a concave surface to a convex surface;
    in the event the transition did not occur before the nozzle continues along the toolpath to the next well, determining that underfilling has occurred; and
    in the event material was deposited for more than a buffer time after the transition occurred, determining that overfilling occurred.

* * * * *